United States Patent
Blanton

[19]

[11] Patent Number: 6,165,159

[45] Date of Patent: Dec. 26, 2000

[54] GAS VENT FOR OSTOMY BAGS

[76] Inventor: Karen J. Blanton, 818 Lusk Rd., Concrete, Wash. 98237

[21] Appl. No.: 09/141,391

[22] Filed: Aug. 27, 1998

Related U.S. Application Data

[60] Provisional application No. 60/057,049, Aug. 27, 1997.

[51] Int. Cl.[7] ........................................... A61F 5/44
[52] U.S. Cl. ................................. 604/333; 604/334
[58] Field of Search .............................. 604/332–345, 604/275–277

[56] References Cited

U.S. PATENT DOCUMENTS

| | | | |
|---|---|---|---|
| 4,211,224 | 7/1980 | Kubach et al. | 128/283 |
| 4,387,712 | 6/1983 | Briggs et al. | 604/333 |
| 4,411,659 | 10/1983 | Jenson et al. | 604/332 |
| 4,449,970 | 5/1984 | Bevan et al. | 604/333 |
| 4,479,818 | 10/1984 | Briggs et al. | 55/385 |
| 4,490,145 | 12/1984 | Campbell | 604/333 |
| 4,516,974 | 5/1985 | Davis | 604/333 |
| 4,723,951 | 2/1988 | Steer | 604/333 |
| 4,875,899 | 10/1989 | Holtermann | 604/333 |
| 4,911,699 | 3/1990 | Fenton | 604/333 |

*Primary Examiner*—John G. Weiss
*Assistant Examiner*—Carie Mager

[57] ABSTRACT

A vent for a latex ostomy bag. A flexible patch is mounted over a plurality of small perforations which are formed in a wall of the bag. The side and bottom edges of the patch are attached adhesively to the surface of the bag so as to form a pouch, with the upper edge of the pouch being free from attachment so as to form an external vent opening. A piece of cotton gauze or other form of porous pad is placed in the pouch, so that accumulated gas in the bag passes into the pouch through the perforations and is vented to the atmosphere via the porous pad. A liquid odor control agent may be applied to the porous pad, and the pad can be periodically removed and replaced without having to replace the entire ostomy bag.

27 Claims, 3 Drawing Sheets

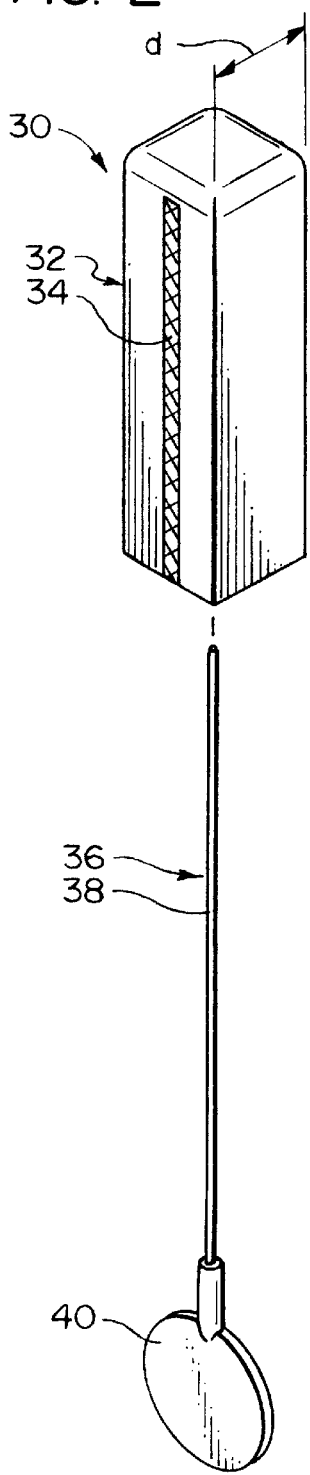
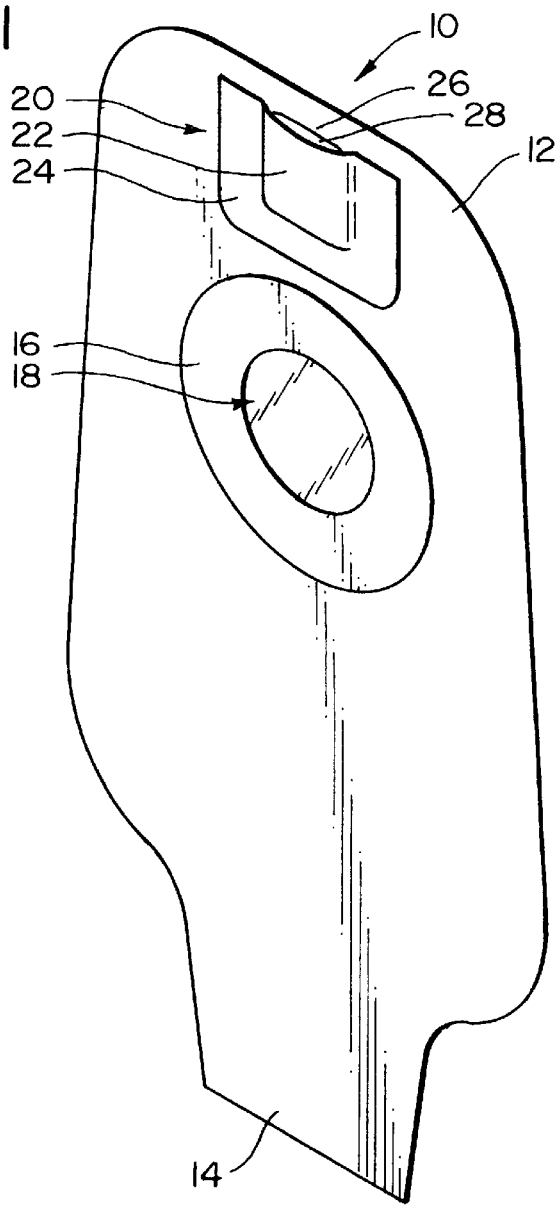

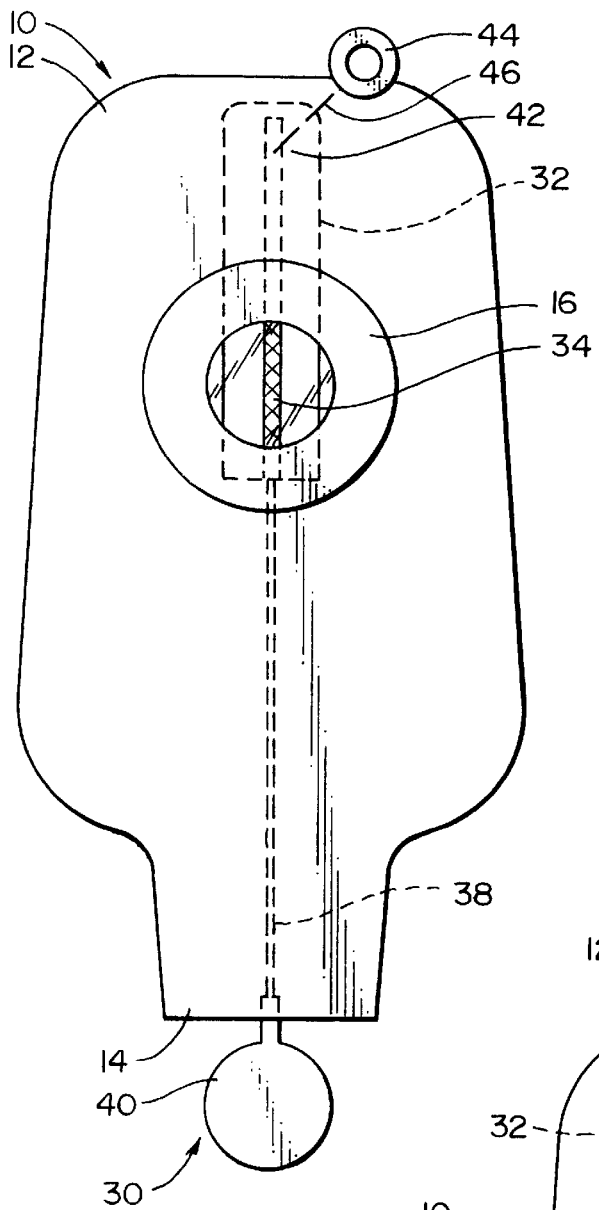
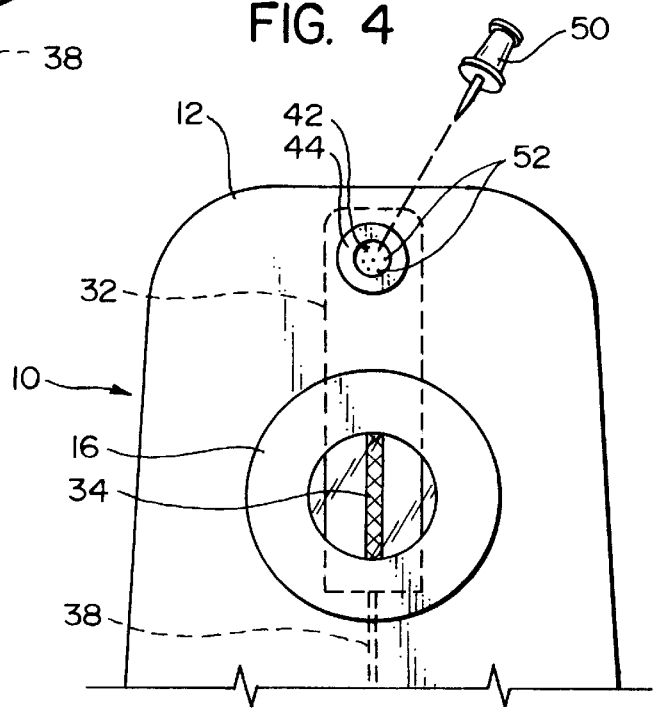

GAS VENT FOR OSTOMY BAGS

This application claims the benefit of U.S. Provisional Application Ser. No. 60/057,049, filed Aug. 27, 1997.

FIELD OF THE INVENTION

The present invention relates generally to ostomy bags, such as colostomy and ileostomy bags, and more particularly, to a vent structure which is adhesively mountable to a latex ostomy bag for relief of accumulated intestinal gas.

RELATED ART

Colostomies and iliostomies are comparatively common surgeries in which the colon and/or a portion of the intestinal tract is removed, ordinarily to remove a tumor or other cancerous growth. In the case of either operation, the discharge end of the patient's truncated intestinal tract is routed to an opening formed in the side of the abdomen, referred to as a "stoma", which resembles a small raised donut on the skin.

An ostomy bag is attached over the stoma to receive the discharge of fecal material from the intestinal tract. Ostomy bags are conventionally constructed of flexible latex or similar material, with a closed upper end and a tapering lower end which can be opened to empty the bag on a periodic basis. A circular adhesive "wafer" is mounted around the intake opening of the bag for attachment to the patient's skin around the stoma.

A persistent and serious problem with conventional ostomy bags is that intestinal gas passes into and accumulates in the bag along with the fecal material. This pressurizes the bag, so that an unsightly bulge develops under the person's clothes. Moreover, unless the pressure is quickly relieved, the pressure can cause the adhesive wafer to detach from the skin around the stoma. To avoid these consequences, the person must excuse themselves immediately upon detecting the gas buildup and proceed to a restroom in order to empty the bag. At a minimum this is a serious nuisance, and under certain circumstances can be extremely embarrassing.

Moreover, certain patients are for one reason or another incapable of monitoring and dealing with this problem in a timely manner. For example, many patients in a nursing home or similar facility may be physically or mentally impaired to the point where they are unable to tend to the problem themselves. Similarly, mentally handicapped persons may be unable to recognize when gas buildup occurs, or understand how to empty the ostomy bag when needed. Since it is usually not feasible to monitor such patients on a constant basis, detachment of the adhesive wafers, spillages, and other problems are very common under such conditions, and represent a constant source of difficulty for care facility staff personnel. Moreover, once the wafer has become detached and contaminated with spilled fecal material, it is usually not possible to use the bag again, and so a fresh one must be put in place. This represents a serious wastage problem, since most ostomy bags are fairly expensive, and are designed to last for about a week in normal use.

Some efforts have been made to provide ostomy bags with built-in vents for relieving gas pressure, but these have not proven successful in all respects. Typically, these bags incorporate a specially molded and/or embedded portion having a porous core or the like through which the gas pressure bleeds to the atmosphere. In part because of the need to mold the extra valve structure into the bag, such bags are prohibitively expensive for many patients, and are simply far too costly for institutional use. Also, such bags often develop venting problems if the porous insert becomes wet during bathing or showering.

Consequently, there exists a need for an apparatus for venting intestinal gas pressure from ostomy bags which is convenient and discrete in operation, and which is economical in use. Furthermore, there exists a need for such an apparatus which does not require the ostomy bag to include a specially molded structure. Still further, there exists a need for such an apparatus in which the porous vent element can be replaced in the event that it becomes wet during use.

SUMMARY OF THE INVENTION

The present invention has solved the problems cited above, and is a vent patch which is adhesively mountable to a conventional latex ostomy bag. This comprises a strip member having (a) a centrally located pouch portion and (b) a peripheral adhesive portion which extends on three sides of the pouch portion. The pouch portion holds a porous pad which is positioned over at least one perforation which is formed in the wall of the ostomy bag. The adhesive portion of the strip mounts the assembly to the bag so that the pouch portion faces in an upward directly, so that gas pressure from within the bag is vented outwardly and upwardly to the atmosphere through the perforation and pad.

A plurality of the porous pads are preferably interchangeably mountable in the pocket area so that the pad can be replaced should it become wet or contaminated, without having to replace the entire assembly or bag. The porous pad is also preferably configured to absorb a liquid deodorizing material so as to remove or camouflage odors in the gas which is vented to the atmosphere.

The present invention also provides a backing assembly which is removably insertable into the interior of the ostomy bag for receiving the end of a pin or similar structure as the perforation or perforations are being formed, so that the end of the pin does not penetrate through to the opposite wall of the bag. The backing member may be a foam, cork, or similar member mounted on the end of a handle member for manipulation to the desired location within the ostomy bag.

The present invention also provides a method for attaching such a vent structure to a conventional, economical latex ostomy bag. Furthermore, the present invention provides an ostomy bag having such a vent mounted thereto.

BRIEF DESCRIPTION OF THE DRAWINGS

FIG. 1 is a perspective view of an ostomy bag having a vent structure in accordance with the present invention mounted adhesively thereto;

FIG. 2 is a perspective view of the penetrable backing member and the handle member to which this is mounted for manual positioning within the interior of the bag during formation of the vent perforations;

FIG. 3 is the first in a sequential series of views showing the formation of the vent perforations and installation of the adhesive vent pouch, this being a plan view showing the positioning of the backing member inside the bag and the attachment of an adhesive reinforcement around the area selected for formation of the perforations;

FIG. 4 is a second in the sequential series of views, this being a plan view similar to FIG. 3 which shows the use of a pushpin to form the plurality of vent perforations through the area which is surrounded by the adhesive reinforcement member, and behind which the backing member is positioned;

DETAILED DESCRIPTION

Figure 5:
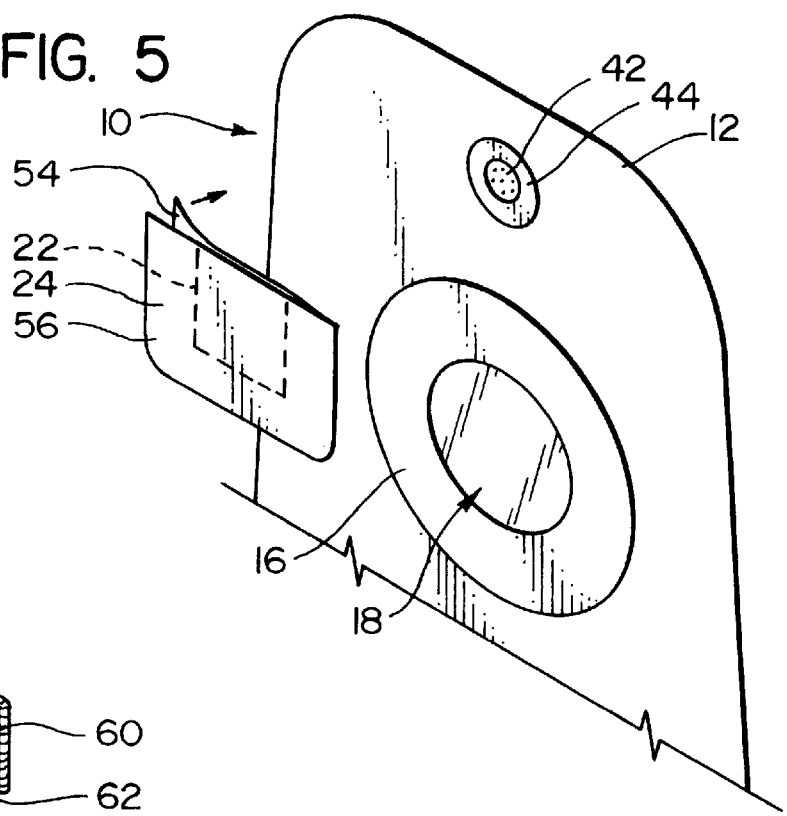
FIG. 5 is the next in the series of views, this being a perspective view of the upper end of the bag with the vent perforations formed therein, and showing the adhesive pouch member positioned in alignment with the vent perforations and having its non-adhesive backing peeled away.

FIG. 1 shows a conventional latex ostomy bag 10 having a closed upper end 12 and a tapered lower end 14 which can be opened for periodically emptying the accumulated fecal material. As was noted above, the bag includes an adhesive wafer 16 which surrounds the inlet opening 18 of the bag, and attaches to the person's abdomen around the stoma. This is more or less the standard configuration for basic, economical ostomy bags which are available from a variety of suppliers, including Hollister, Inc. (Libertyville, Ill.), or Bristol-Myer Squibb Co., and others.

FIG. 1 also shows an adhesive vent assembly 20 in accordance with the present invention, attached to the inner surface of the ostomy bag (i.e., the surface facing towards the person's body), above the inlet opening 18. As can be seen and as will be described in greater detail below, the vent assembly includes the central pouch area 22 having an adhesive border 24 along three sides thereof. The forth side is free from attachment to the surface of the ostomy bag, so as to form an upper opening 26 which receives a porous pad 28, through which the intestinal gasses exiting the bag pass as they are vented to the atmosphere.

FIG. 2, in turn, shows the backing assembly 30 for forming the vent perforations in the upper end of the ostomy bag. The backing assembly includes a bed portion 32 formed of styrofoam, cork, or other suitable material which is easily penetrable by the point of a pin member, such as a conventional pushpin. Suitable dimensions for the bed are approximately 4¼" long by ¾" square when constructed of styrofoam, although the dimensions for any particular embodiment are a matter of design choice. The purpose of the bed is to provide a backing behind the plastic wall of the bag, into which the point of the pin member can penetrate while forming the perforations, without poking a hole through the opposite wall of the bag. Accordingly, the bed 32 has a thickness "d" which is sufficient to prevent the tip of the pin member from penetrating to the opposite side of the bed, given the length of the pin member and the resilience of the bed material. Also, the surface along at least one side of the bed member is preferably provided with a colored centering line 34 to assist the user visually in properly aligning of the assembly.

Although the backing assembly may be a unitary piece having sufficient length to reach from the lower opening of the ostomy bag to its upper end, the actual bed member 32 is preferably a comparatively short piece which is mounted on the end of the an extension handle 36, as shown in FIG. 2. The extension handle includes a comparatively long wire rod section 38 which is inserted into the penetrable material of the bed member 32 (e.g., 1"), and a knob or disk 40 at its lower end by which the assembly may be manipulated. This configuration has the advantage of being easier to manipulate through the narrow opening 14 at the bottom of the ostomy bag (due to the thinness of the wire rod 38), and it is also more pleasant to work with and generates less waste than in the case of a unitary piece or "stick" of Styrofoam or other penetrable material.

FIGS. 3–6 present a sequence of views illustrating a method in accordance with the present invention by which the adhesive vent assembly is installed on a conventional ostomy bag.

As can be seen in FIG. 3, the first step is to place the bag on a flat, clean work surface and then insert the backing assembly 30 through the open lower end 14 of the ostomy bag 10, so that the bed member 32 is positioned inside the bag near its upper end 12. Viewing the colored centering line 34 through the transparent material of the bag, the operator positions the bed beneath a suitable location 42 above the wafer 16, and then places a circular, adhesive reinforcing member 44 around this, as indicated by dotted line 46 in FIG. 3. The reinforcement member may suitably be a self-adhesive "ring", formed of fabric, plastic, paper or other tear-resistant material.

As can be seen in FIG. 4, the operator then employs a pushpin 50 or similar pin member to form several (e.g., three) perforations 52 through the latex of the wall of the ostomy bag in the area 42 surrounded by the reinforcement ring 44. The use of several small-diameter (e.g., approximately 1 mm diameter or less) perforations, as opposed to a single large-diameter opening, has the advantage of moderating the flow of gas into the pouch, and also limits the entry of liquid and/or fecal material which might soak the pad member.

As the penetrations are formed, the pin penetrates into the underlying bed member 32, which prevents the tip of the pin from poking holes in the opposite side of the bag. The reinforcement ring, in turn, prevents any resulting tears from developing which might extend beyond the immediate area 42 of the perforations.

Having completed the step shown in FIG. 4, the operator withdraws the backing assembly from the interior of the ostomy bag, and then removes the non-adhesive backing 54 from the back of the pouch strip 56. Preferably the backing sheet is formed in two pieces which are color-coded (e.g., blue on the left, red on the right) to ensure proper orientation of the adhesive strip, i.e., with the open edge of the pouch pointed upwardly. Hence, to install the strip, the operator first removes the backing sheet on one side and presses that side of the strip against the surface of the bag, with the vent perforation area 42 positioned more or less centrally within the pocket area 22. The other backing sheet is then removed and the other side of the strip is pressed against the bag, and then both edges of the strip are pressed smooth.

The strip is suitably formed of vinyl material, similar to that used in conventional self-adhesive bandages, with a waterproof adhesive border which extends around three sides of the pocket area. The material is preferably soft and resiliently flexible so that it conforms to the surface of the bag, and also for enhanced user comfort. Moreover, the material is preferably transparent or translucent so that the perforation area and reinforcement ring can be seen through the strip during positioning. Other flexible, adhesive strip materials may be used, so long as these form the pocket area 22 over the vent perforations, with a free upper edge which permits venting of the gas and removable insertion of the porous pad.

Figure 6:
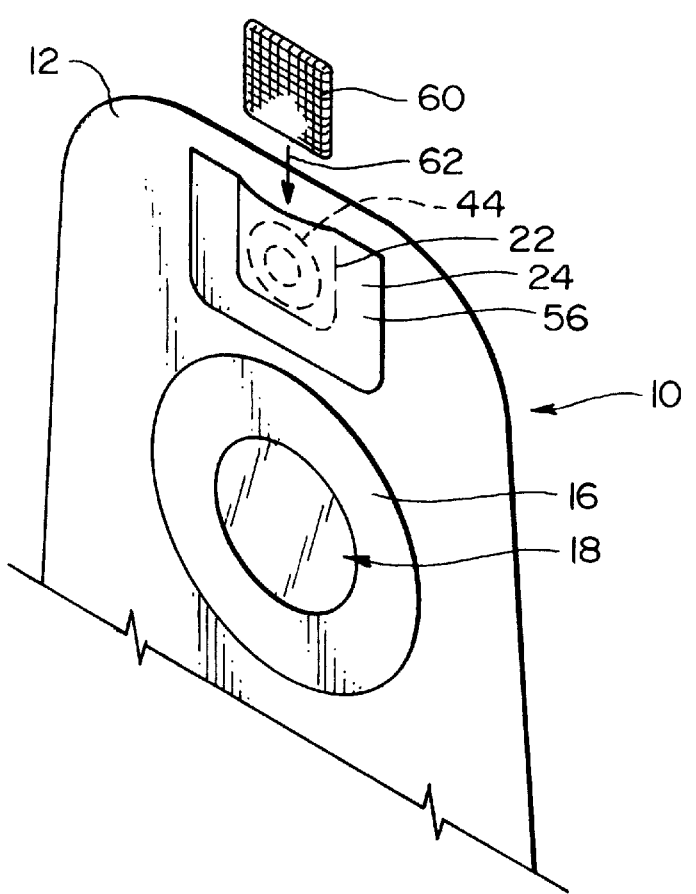
FIG. 6 is the last of the sequential series of views, this being a perspective view of the upper end of the bag similar to FIG. 5, showing the adhesive pouch strip having been mounted to the bag over the vent perforations, and the porous vent pad then being inserted into the open upper end of the pouch strip so that the gas will pass through this upon being vented to the atmosphere.

As is shown in FIG. 6, the operator next inserts the porous pad 60 into the pocket area between the surface of the bag and strip 56, in the direction indicated by arrow 62. The porous pad 60 may be formed of cotton gauze, or a similar porous, preferably absorbent material. Suitable dimensions for the patch when constructed of cotton gauze are approximately ¾" square by ¹⁄₁₆" thick (with the pocket area being sized accordingly), although other sizes may be used in various embodiments depending on the type of porous/absorbent material supplied and other design factors.

After the complete vent patch has been installed the bag is mounted against the person's body using the adhesive wafer 16, so that as intestinal gas accumulates in the bag, this escapes in a gradual manner through the perforations 52 and pad 60. If the person needs to vent an additional amount of gas from the bag, this is accomplished by simply pressing the bag gently against the side of the body, under the arm. The venting is silent, and moreover, the porous pad 60 can be saturated with a deodorizing material to reduce or eliminate any odors associated with the gas; an example of a liquid deodorant material suitable for this purpose is that sold as Banish II™ appliance deodorant, available from Smith & Nephew United, Inc., Largo, Fla.

The porous, absorbent pad also prevents any inadvertent escape of fecal material through the vent assembly.

The porous pad 60 is removable so that this can be replaced periodically with identical units, in order to extend the surface life of each bag. For example, should the pad become water-soaked during showering/bathing, this can simply be removed and replaced with a fresh pad. Also, the liquid deodorant material can be replenished periodically, as needed.

It is to be recognized that various alterations, modifications, and/or additions may be introduced into the constructions and arrangements of parts described above without departing from the spirit or ambit of the present invention as defined by the appended claims.

What is claimed is:

1. A vented ostomy bag, comprising:
    a bag member for attachment to an abdominal stoma; and
    a vent assembly mounted to an upper portion of said bag member, said vent assembly comprising:
        a patch member having an interior portion in fluid communication with an interior of said bag member so as to define a vent pouch, said patch member comprising:
            first and second side edges and a bottom edge of said patch member which are attached to a surface of said bag member so as to define an interior of said vent pouch; and
            at least a portion of an upper edge of said patch member which is free from attachment to said surface of said bag member so as to define an external opening of said vent pouch; and
        a porous pad member received in said interior of said vent pouch;
    whereby gas received in said bag member will pass into said vent pouch and be vented out said external opening via said porous pad member.

2. The ostomy bag of claim 1, wherein said side edges and bottom edge of said patch member are adhesively attached to said surface of said bag member.

3. The ostomy bag of claim 1, wherein said patch member is formed of a soft, resiliently flexible sheet material which flexes in conformity with said surface of said bag member.

4. The ostomy bag of claim 3, wherein said patch member is mounted to an inner side of said bag member above an opening of said bag which is attachable to an abdominal stoma.

5. The ostomy bag of claim 1, wherein said porous pad member comprises:
    a porous pad member which is inserted into said interior of said vent pouch through said opening in said upper portion thereof.

6. The ostomy bag of claim 5, wherein said porous pad member is interchangeably replaceable with other pad members which are insertable in said vent pouch.

7. The ostomy bag of claim 6, wherein each said pad member comprises:
    a pad member formed of porous gauze material.

8. The ostomy bag of claim 1, further comprising:
    at least one opening formed through said surface of said bag member within an area of said surface which is bounded by said attached side edges and bottom edge of said patch member, so as to establish fluid communication between said interior of said bag member and said interior of said vent pouch.

9. The ostomy bag of claim 8, wherein said at least one opening through said surface of said bag member comprises:
    a plurality of small-diameter perforations formed through said area of said surface which is bounded by said side edges and bottom edge of said patch member.

10. The ostomy bag of claim 8, further comprising:
    an annular reinforcement member mounted to said surface of said bag member around said at least one opening therethrough, so as to prevent tears from starting at said at least one opening and spreading outside of said area bounded by said side edges and bottom edge of said patch member.

11. A vent assembly mountable to an ostomy bag having a bag member for attachment to an abdominal stoma, said vent assembly comprising:
    a patch member which is mountable to an upper portion of said bag member so that an interior portion of said patch member is in fluid communication with an interior of said bag member so as to define a vent pouch, said patch member comprising:
        means for mounting said patch member to said bag member so that first and second side edges and a bottom edge of said patch member are attached to a surface of said bag member so as to define an interior of said vent pouch, and so that at least a portion of an upper edge of said patch member is free from attachment to said surface of said bag member so as to define an external opening of said vent pouch;
    a porous pad member which is receivable in said interior of said vent pouch; and
    an external opening formed in an upper portion of said vent pouch;
    whereby gas received in said bag member will pass into said vent pouch and be vented out said external opening via said porous pad member.

12. The vent assembly of claim 11, wherein said means for mounting said patch member to said bag member comprises:
    an adhesive layer for attaching said side edges and bottom edge of said patch member to said surface of said bag member.

13. The vent assembly of claim 11, wherein said patch member is formed of a soft, resiliently flexible material which flexes in conformity with said surface of said bag member.

14. The vent assembly of claim 11, wherein said porous pad member is interchangeably replaceable with other pad members which are insertable in said vent pouch.

15. The vent assembly of claim 14, wherein each said pad member comprises:

a pad member formed of porous gauze material.

16. The vent assembly of claim 11, further comprising:

means for forming at least one opening through said surface of said bag member within an area which is bounded by said attached side edges and bottom edge of said patch member, so as to establish fluid communication between said interior of said bag member and said interior of said vent pouch.

17. The vent assembly of claim 16, wherein said means for forming at least one opening through said surface of said bag member comprises:

a pin member for piercing said surface of said bag member so as to form a plurality of small-diameter perforations through said area of said surface which is bounded by said side and bottom edges of said patch member.

18. The vent assembly of claim 16, further comprising:

an annular reinforcement member which is mountable to said surface of said bag member around at least one opening which is formed therethrough so as to prevent tears from starting at said opening and spreading outside of said area bounded by said side edges and bottom edge of said patch member.

19. A vent assembly which is mountable to an ostomy bag having a bag member for attachment to an abdominal stoma, said vent assembly comprising:

a soft, resiliently flexible patch member which is mountable to said ostomy bag, said patch member having an adhesive layer for attaching first and second side edges and a bottom edge of said patch member to a surface of said bag member so as to define an interior of a vent pouch, and so that at least a portion of an upper edge of said patch member is free from attachment to said surface of said bag member so as to define an external opening of said vent pouch;

means for forming at least one opening through said surface of said bag member in an area bounded by said side edges and bottom edge of said patch member, so as to establish fluid communication between an interior of said bag member and said interior of said vent pouch;

an annular reinforcement member mountable to said surface of said bag member around said at least one opening therethrough, so as to prevent tears from starting at said opening and spreading outside of said area bounded by said edges of said patch member; and a replaceable porous gauze pad which is receivable in said interior of said vent pouch;

wherein when said vent assembly is connected to said bag member, gas received in said bag member will pass into said vent pouch and be vented out said external opening via said porous gauge pad member.

20. A method for forming a vent for an ostomy bag, comprising:

providing a bag member for attachment to an abdominal stoma;

mounting a patch member to an upper portion of said bag member so that an interior of said patch member is in fluid communication with an interior of said bag member and defines a vent pouch, the step of mounting said patch member to said upper portion of said bag member comprising:

mounting said patch member to said bag member so that first and second side edges and of bottom edge of said patch member are attached to a surface of said bag member so as to define an interior of said vent pouch, and so that at least a portion of an upper edge of said patch member is free from attachment to said surface of said bag member so as to define an external opening of said vent pouch; and placing a porous pad member in said interior of said vent pouch;

whereby gas received in said bag member will pass into said vent pouch and be vented out said external opening via said porous pad member.

21. The method of claim 20, wherein the step of mounting said patch member to said bag member comprises:

adhesively attaching said side edges and bottom edge of said patch member to said surface of said bag member.

22. The method of claim 20, wherein the step of mounting said patch member to said bag member comprises:

forming said patch member of a soft, resiliently flexible material which flexes in conformity with said surface of said bag member.

23. The method of claim 20, wherein the step of placing a porous pad member in said interior of said vent pouch comprises:

said porous pad member being formed for interchangeable replacement by other pad members in said vent pouch.

24. The method of claim 20, wherein the step of mounting said patch member to said bag member further comprises:

forming at least one opening through said surface of said bag member within an area which is bounded by said attached side edges and bottom edge of said patch member, so as to establish fluid communication between said interior of said bag member and said interior of said vent pouch.

25. The method of claim 24, wherein the step of forming at least one opening through said surface of said bag member comprises:

piercing said surface of said bag member with a pin member so as to form a plurality of small-diameter perforations through said area of said surface which is bounded by said side edges and bottom edge of said patch member.

26. The method of claim 25, wherein the step of forming said plurality of perforations in said surface of said bag member comprises:

inserting a penetrable bed member into said interior of said bag member behind said surface of said bag member in said area bounded by said side edges and bottom edge of said patch member, said bed member having sufficient thickness to be penetrated by said pin member without allowing said pin member to pierce an opposite surface of said bag member.

27. The method of claim 24, further comprising:

mounting an annular reinforcement member to said surface of said bag member around said at least one opening therethrough so as to prevent tears starting at said at least one opening and spreading outside of said area bounded by said side edges and bottom edge of said patch member.

* * * * *